United States Patent [19]

Blackwell

[11] 4,094,894

[45] June 13, 1978

[54] PROCESS OF PURIFYING ALIPHATIC ISOCYANATES

[75] Inventor: Julian Theron Blackwell, Wilmington, Del.

[73] Assignee: E. I. Du Pont de Nemours and Company, Wilmington, Del.

[21] Appl. No.: 780,345

[22] Filed: Mar. 23, 1977

[51] Int. Cl.² .......................................... C07C 119/042
[52] U.S. Cl. ............................................... 260/453 SP
[58] Field of Search .................................. 260/453 SP

[56] References Cited

U.S. PATENT DOCUMENTS

| | | | |
|---|---|---|---|
| 2,885,423 | 5/1959 | Spiegler | 260/453 SP |
| 3,465,023 | 9/1969 | Kamal | 260/453 PH |

*Primary Examiner*—Dolph H. Torrence

[57] ABSTRACT

Aliphatic isocyanates are purified by mixing with a finely divided alkali metal carbonate at 180° to 235° C.

11 Claims, No Drawings

PROCESS OF PURIFYING ALIPHATIC ISOCYANATES

This invention relates to a process of purifying commercially produced aliphatic isocyanates.

Aliphatic isocyanates are manufactured commercially by the reaction of phosgene and an organic amine. One such process is described in U.S. Pat. No. 3,574,695, issued to Grant et al. Apr. 13, 1971. Another such process is described in U.S. Pat. No. 3,465,023, issued Sept. 2, 1969 to Kamal. The reaction product of phosgene and the organic amine contains aliphatic isocyanate and varying amounts of hydrogen chloride, present as primary carbamyl chloride

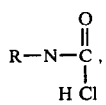

and secondary carbamyl chloride

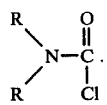

Distillation and conventional separation procedures remove only a portion of these hydrolyzable chlorine containing impurities. Some commercial operations have subjected the reaction product to multiple distillation processes in order to lower the amount of these impurities in the final product, but the procedure is expensive since multiple distillation requires the use of more energy, and since multiple distillation increases the amount of tars and other high molecular weight reaction products formed, the yield of the desired product is also lowered.

Aliphatic polyisocyanates are widely used in the formation of polyurethane coatings and foams. Polyurethanes formed using pure aliphatic polyisocyanates are transparent and colorless, or by the addition of suitable colorants may be made in pastel shades, whereas the polyurethanes formed from aromatic polyisocyanates possess an inherent tendency to discolor.

A polyurethane polymer is formed by the reaction of the aliphatic diisocyanate and a polyol. Some difficulty has been encountered in the preparation of polyurethane coatings and foams of uniform quality and color. Some of this difficulty can be traced to the fact that different batches of the same aliphatic diisocyanate react at different rates with the same polyol under the same conditions. It has been determined that this variable reactivity is at least partly caused by varying concentrations of one or more impurities having hydrolyzable chlorine which are present in the aliphatic isocyanate component of the reaction mixture. The hydrolyzable chlorine containing components of aliphatic isocyanates act as poisons and apparently generate other compounds which act as poisons for the catalysts that are employed when the aliphatic isocyanate is reacted with a polyol; thus removal of the hydrolyzable chlorine would allow the polyurethane formation reaction to proceed in a more predictable manner. Furthermore, the variable concentration of hydrolyzable chlorine in the isocyanate results in polyurethanes of variable color, so removal of hydrolyzable chlorine is also beneficial for this reason.

The hydrolyzable chlorine content present as an impurity in an isocyanate is determined by the following procedure which is a modification of ASTM D 1638:

1. Weigh sufficient sample to contain 1–4 mg hydrolyzable chlorine into a clean, dry 400-ml beaker.
2. Add 250 ml of isopropyl alcohol.
3. Cover with a clean watch glass and agitate on a magnetic stirrer for 10–15 min.
4. Transfer the beaker from the stirrer to a steam bath for 30 min.
5. Wash down the sides of the beaker with isopropyl alcohol and cool to room temperature by means of an ice bath.
6. Add 10 ml 1:1 nitric acid to the sample.
7. Titrate with 0.025 N aqueous silver nitrate and determine end-point potentiometrically using silver and calomel electrodes.

It has been proposed to remove hydrolyzable chlorine from an aliphatic isocyanate by treating the isocyanate with an aqueous solution of a weak base. See U.S. Pat. No. 3,465,023, especially column 5, lines 21 through 47. Treatment of aromatic diisocyanate — specifically toluene diisocyanate — by distillation from lime as a method of removing hydrolyzable chlorine has also been proposed. See "Industrial and Engineering Chemistry," August 1959, pages 929 through 934 — specifically column 1 of page 931.

The present invention provides a process of purifying an aliphatic isocyanate, i.e., reducing (lowering) the hydrolyzable chlorine content of an aliphatic isocyanate containing hydrolyzable chlorine. The process comprises mixing finely divided dry alkali metal carbonate, or mixtures of alkali metal carbonates, with the aliphatic isocyanate at a temperature between 180° and 235° C.

The reaction time is not critical, for some reduction in hydrolyzable chlorine content occurs very promptly after the components are brought together at 180° to 235° C, and even after 2 hours at this temperature there may remain a small amount of hydrolyzable chlorine in the aliphatic isocyanate. The usual reaction time is about 15 minutes to about 2 hours.

The preferred alkali metal carbonate is sodium carbonate, although potassium and lithium carbonates are also satisfactory.

The amount of alkali metal carbonate mixed with the aliphatic isocyanate is not critical. If the amount is less on a stoichiometric basis than the amount of hydrolyzable chlorine present, then not all of the removable hydrolyzable chlorine will be removed. It is usually desirable to reduce the hydrolyzable chlorine level as low as possible; and accordingly it is usually desirable to add at least a stoichiometric amount of the alkali metal carbonate. It is believed the reaction takes place primarily at the surface of the alkali metal carbonate, so a moderately large excess of alkali metal carbonate is usually employed.

In order to achieve significant reaction of the hydrolyzable chlorine and the alkali metal carbonate it is critical that the alkali metal carbonate be dry and finely divided. The carbonate may be finely divided by grinding in an air mill provided that the relative humidity is controlled so that the product absorbs only minor amounts of atmospheric moisture. The degree of fineness is not critical, but best results are obtained with alkali metal carbonate in which most of the particles are not greater than 5 microns in diameter.

One preferred method of obtaining dry finely divided alkali metal carbonate is to grind it in a closed ball mill containing aliphatic isocyanate. The aliphatic isocyanate keeps moisture from the air from being absorbed by the alkali metal carbonate.

The carbonate may also be ground in another inert organic liquid, then added to the aliphatic isocyanate. Other suitable organic liquids include ortho dichlorobenzene, xylene, heptane, and chlorobenzene.

After the treatment has been completed, the isocyanate is separated from the alkali metal carbonate and resulting alkali metal chloride. Many suitable methods are available, for example, the separation may be effected by filtration, distillation or centrifugation.

The process of the present invention may be carried out using any aliphatic isocyanate, including 4,4'- and 2,4'-methylenebis(cyclohexyl isocyanate); 1,6-hexamethylene isocyanate; 2,2,4'-trimethyl-1,6-hexamethylene diisocyanate; 1-isocyanato-3-isocyanatomethyl-3,5,5-trimethyl cyclohexane; and hexahydrotoluene diisocyanate.

In the following examples all parts and percentages are by weight unless otherwise specified, and all temperatures are in degrees centigrade.

EXAMPLES

Example 1

Commercial 4,4'-methylenebis(cyclohexylamine) is phosgenated in orthodichlorobenzene. The orthodichlorobenzene is then removed by fractional distillation. The excess phosgene and most of the combined HCl is removed by this fractionation leaving crude 4,4 methylenebis(cyclohexyl isocyanate) containing 2360 ppm of hydrolyzable chlorine.

Some of this crude 4,4'-methylenebis(cyclohexyl isocyanate) was ball milled in a one quart ball mill with 2 wt. % anhydrous $Na_2CO_3$ for about 2½ days at 25° C. The product was a dispersion of finely divided $Na_2CO_3$ in 4,4'-methylenebis(cyclohexyl isocyanate) liquid.

Then 510 g of this 2% dispersion of $Na_2CO_3$ in 4,4'-methylenebis(cyclohexyl isocyanate) and a magnetic stirring bar were placed in a 1 liter distilling flask attached to a low-pressure-drop spinning band column and fractionated at about 1 mm Hg head pressure.

The ortho-dichlorobenzene fraction and the monoisocyanate fraction were removed over a 40 minute period (pot temperature about 190°–200° C) at a 2/1 reflux ratio and then the product cut was distilled over with total takeoff.

The product fraction (about 88% yield) contained no detectable hydrolyzable chlorine (<5 ppm).

A control run was made omitting the $Na_2CO_3$. The product fraction showed 340 ± 20 ppm of hydrolyzable chlorine.

Example 2

Another sample of the crude 4,4'-methylenebis(cyclohexyl isocyanate) (450 g) was ball milled with anhydrous $Na_2CO_3$ (150 g) to yield a 25% dispersion of $Na_2CO_3$ in 4,4'-methylenebis(cyclohexyl isocyanate) liquid after 40 hours ball milling. This dispersion was used in several purification runs.

To a 1 liter flask with a low-pressure-drop distilling head was added 12 g of the dispersion discussed above and 141 g of crude 4,4'-methylenebis(cyclohexyl isocyanate). This gave a mixture containing 3 g $Na_2CO_3$ (finely divided) in 150 g of crude 4,4'-methylenebis(cyclohexyl isocyanate). The flask was fitted with a magnetic stirring bar and a thermometer. Stirring was initiated and rapid heating using a heating mantle was begun. The product distilled at 160° ± 5° C pot temperature in about 4 minutes. This represents its heat treatment cycle with the fresh $Na_2CO_3$ dispersion. The product contained 163 ± 14 ppm of hydrolyzable chlorine after fractionation in a low-pressure-drop spinning band column.

Example 3

Using the same equipment, samples, and technique of Example 2, a run was made at 200° C for 1 hour followed by rapid distillation at about 175° C. The product fraction showed no detectable hydrolyzable chlorine (<5 ppm).

Example 4

Following the procedure of Example 3 except that the mixture was held at 200° ± 5° C for 0.5 hours and then worked up and analyzed, the product showed no detectable hydrolyzable chlorine in the product fractions.

Examples 5 and 6

Following the procedure of Example 3 using holding times at 200° ± 4° C of 15 minutes and 8 minutes produced products with 9 ppm and 41 ppm, respectively. The dispersion of Example 2 was 6 days old when these examples were run.

Example 7

Following the procedure of Example 3 using the 6 day old dispersion at 1% $Na_2CO_3$ in crude 4,4'-methylenebis(cyclohexyl isocyanate) (instead of the usual 2%) gave a product containing no detectable hydrolyzable chlorine (<5 ppm) after a treatment of 0.5 hr. at 203° ± 5° C.

Example 8

Substantially the same results as those shown in Examples 1–7 may be obtained using similar amounts of potassium carbonate or lithium carbonate.

We claim:

1. A process for purifying an aliphatic isocyanate containing hydrolyzable chlorine which comprises mixing finely divided dry alkali metal carbonate with the aliphatic isocyanate containing the hydrolyzable chlorine, at a temperature between 180° and 235° C.

2. The process of claim 1 in which the alkali metal carbonate is selected from the class consisting of sodium carbonate, potassium carbonate, and lithium carbonate.

3. The process of claim 1 in which the finely divided dry alkali metal carbonate is formed by grinding the metal carbonate in the presence of the aliphatic isocyanate.

4. The process of claim 1 in which the alkali metal carbonate is ground in aliphatic isocyanate and then added to the impure isocyanate to be treated.

5. The process of claim 1 in which the carbonate is finely divided by grinding it in another inert organic liquid.

6. The process of claim 1 which includes the additional step of separating the aliphatic isocyanate from the reaction product of the carbonate and the hydrolyzable chlorine.

7. The process of claim 6 in which the separation is accomplished by distillation.

8. The process of claim 6 in which the separation is accomplished by filtration.

9. The process of claim 1 in which the aliphatic isocyanate is 4,4'-methylenebis(cyclohexyl diisocyanate).

10. The process of claim 9 in which sodium carbonate is the alkali metal carbonate.

11. The process of claim 1 in which most of the finely divided dry alkali metal carbonate particles have a diameter of no greater than 5 microns.

* * * * *